United States Patent
Weckstrom et al.

(10) Patent No.: US 6,694,800 B2
(45) Date of Patent: Feb. 24, 2004

(54) GAS ANALYZER USING THERMAL DETECTORS

(75) Inventors: Kurt Weckstrom, Espoo (FI); Mika Hietala, Espoo (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 10/392,660

(22) Filed: Mar. 20, 2003

(65) Prior Publication Data

US 2003/0177814 A1 Sep. 25, 2003

(30) Foreign Application Priority Data

Mar. 22, 2002 (EP) .............................. 02396036

(51) Int. Cl.$^7$ .............................. G01N 25/00; G01J 5/02
(52) U.S. Cl. ...................... 73/25.01; 250/345
(58) Field of Search .............. 73/25.01, 31.05; 250/343, 345, 339.13

(56) References Cited

U.S. PATENT DOCUMENTS

| | | |
|---|---|---|
| 4,772,790 A | 9/1988 | Aldridge |
| 5,012,813 A | 5/1991 | Pompei et al. |
| 5,081,998 A | 1/1992 | Yelderman et al. |
| 5,153,436 A * | 10/1992 | Apperson et al. ............ 250/345 |
| 5,296,706 A | 3/1994 | Braig et al. |
| 5,445,158 A | 8/1995 | Pompei |
| 5,542,285 A | 8/1996 | Merilainen et al. |
| 5,747,809 A * | 5/1998 | Eckstrom .................... 250/345 |
| 5,793,044 A * | 8/1998 | Mace et al. ................. 250/343 |
| 5,886,348 A * | 3/1999 | Lessure et al. ......... 250/339.13 |
| 6,277,081 B1 | 8/2001 | Susi et al. |
| 6,599,253 B1 * | 7/2003 | Baum et al. ................. 600/532 |
| 2002/0026822 A1 * | 3/2002 | Reading et al. ............ 73/31.05 |

FOREIGN PATENT DOCUMENTS

EP 692 702 1/1996

OTHER PUBLICATIONS

Applications of Thermoelectric Infrared Sensors (Thermopiles): Gas Detection by Infrared Absorption; NDIR, Jurgen Schilz PhD, PerkinElmer Optoelectronics Thermophysica Minima, Version 22, Aug. 2000, pp. 2–11.
Derwent Publication Ltd., Abstract XP–002215151 & JP 11 326250 (Shinagawa Fire Brick), Nov. 26, 1999.

* cited by examiner

Primary Examiner—Hezron Williams
Assistant Examiner—Jay L Politzer
(74) Attorney, Agent, or Firm—Andrus, Sceales, Starke & Sawall, LLP (57) ABSTRACT

The invention relates to a gas analyzer comprising a measuring volume (6) for a sample gas mixture (G), a radiation source (1) for providing a beam (20) of electromagnetic radiation to pass said measuring volume, a heat sink (4) for said radiation source, at least one thermopile detector (9), at least one optical bandpass filter (10), electrical contact pins (12) for signal(s) in the housing of said detector, a thermal mass formed of a material having high thermal conductance. Said thermal mass has a cavity (21) and an outer surface (22), surrounding at least said detector housing in the cavity, being in contact with said detector housing, and extending towards the radiation source. There is a thermal barrier between the heat sink (4) and the thermal mass (8, 16). The gas analyzer further comprises electrical wires (15), which are composed of materials and having dimensions producing an overall thermal conductance substantially lower than that of said electrical contact pins. Said wires are connected with the electrical contact pins either directly or indirectly, and enclosed in the thermal mass together with said detector housing(s), and extend from the cavity through the thermal mass (8, 16) to the outside thereof.

26 Claims, 3 Drawing Sheets

GAS ANALYZER USING THERMAL DETECTORS

CROSS REFERENCE TO RELATED APPLICATION

The present application claims priority from European Patent Application No. 02396036.2, filed Mar. 22, 2002.

BACKGROUND OF THE INVENTION

The invention relates to a gas analyzer comprising: a measuring volume having connections for input and output flow of a sample gas mixture, at least one gas component of which is to be analyzed for determining its concentration in said mixture, and having first and second ends transparent to radiation; a radiation source for providing a beam of electromagnetic radiation having a wavelength range, said beam approaching collimation and being directed to pass said measuring volume through the first and second ends thereof; a heat sink for said radiation source; at least one thermal detector having an active radiation detecting sensor element within at least one detector housing and receiving the radiation exiting said measuring volume, said thermal detector having a reference sensor element within the same detector housing and protected from said radiation, said thermal detector generating an output signal indicative of a property of said at least one gas component of said mixture in the measuring volume; at least one optical bandpass filter between said active radiation detecting sensor element and said radiation source; electrical contact pins in said at least one detector housing for the output of said signal(s); a thermal mass formed of a material having high thermal conductance, said thermal mass: having a cavity and an outer surface, surrounding at least said detector housing in the cavity, being in contact with said detector housing, and extending towards the radiation source; and a thermal barrier between the heat sink and the thermal mass.

Thermal detectors, typically thermopile detectors are used in gas analyzers among other things owing to their capability of DC (Direct Current) measurement, which facilitates a cost-effective construction of the measurement system. In these gas analyzers the thermopile detector measures the infrared absorption of a gas introduced to a sampling chamber or a sampling volume, after which the concentration of the gas component or the gas components of interest is/are determined from the measured absorption. The useful wavelength range of thermopile detectors is suitable for infrared measurements, since their absorption bands in the wavelength region 3 $\mu$m–10 $\mu$m fall within the required spectral sensitivity wavelength range for the detector. Moreover, thermopiles have a high sensitivity and good linearity and they are cost effective components.

A characteristic of a thermopile detector is that a thermal gradient in its external housing, noticeable especially in small analyzers with small thermal mass, will cause an offset error in the detector signal, which degrades measurement accuracy. The thermopile is a very sensitive detector containing a plurality of thermocouple junctions. In a typical analyzer it has been measured that the signal change corresponding to the absorption caused by 0.1% by volume of $CO_2$ in a sample gas is about 2 $\mu$V. The temperature difference in the thermopile detector would then be only about 0.13 mK. It is therefore easy to understand that even small temperature gradients in the thermopile housing may cause considerable measurement errors. Similar errors also occur with a change of the external housing temperature after, e.g., a cold start-up of the analyzer or due to a change in the ambient temperature.

With reference to the patent U.S. Pat. No. 4,772,790 a gas analyzer is described where a number of thermocouples connected to form groups of thermopiles are used as the detector. The first set of thermopile groups is arranged so as to receive the radiation at their inner junctions to form hot junctions, whereas the outer junctions shielded accordingly form cold junctions of this first set. The thermocouples of the second set of thermopile groups, having the same number of shielded thermocouples as the first set, are electrically connected in series with the first set, whereupon the electrical current caused by the EMFs from the first set because of the radiation creates inverted cold as well as hot junctions in the second set of thermopile groups with opposite EMFs to those of the thermocouples of the first set. All of the thermocouples with their hot and cold junctions are positioned on a single substrate of a heat-conductive insulator material. The analyzer is further provided with a highly heat conductive section, which is in contact with the ambience and has a thermal mass substantially greater than that of the housing so that it acts as a large area heat sink. The heat-conductive substrate of the thermopiles is connected with the conductive section using a heat conductive material. Further the radiation source is thermally insulated from the heat conductive section by the wall of the sample cell made of plastic or the like. This seems to be the conventional compensation method. In this construction there is a need for additional dark junctions, which reduces the space for the sensitive area of the detector. The leads from the detector housing are directly connected to the conductive pads of a printed circuit board in contact with ambience, too. As a consequence, even an extremely small change of the temperature from the ambience would cause a considerable thermal gradient on the substrate and so within the thermopile array. Especially in a small analyzer such a gradient could induce an offset in the signal, which would not necessarily be completely compensated by the shielded junctions. For modern semiconductor thermopiles bonded to the base plate of the housing this is especially true. Under a steady state condition, in which the non-shielded hot junctions are receiving a constant radiation, there may exist even a temporal thermal drift, whereupon the DC-signal from the detector varies with time, leading to measurement inaccuracies.

The patent U.S. Pat. No. 5,081,998 discloses a gas analyzer where a group of thermocouples is connected in series and paired so that the first thermopile and the second thermopile is in opposed relationship to each other on a common ceramic substrate. The first thermopile is electrically connected to the second thermopile in series opposition to subtract the output signals from each other, and further at least a first neutral density, i.e. attenuation filter with a different transmission coefficient as compared to a second or lacking neutral density filter are positioned in front of the thermopile detectors so that the first neutral density filter affects the hot junctions of the first thermopile and the second neutral density filter or its absence affects the hot junctions of the second thermopile, whereupon these two thermopile detectors are "optically stabilized". The thermopile detectors are further preceded by one or several analytical bandpass filters and a reference bandpass filter for passing desired wavelengths in the optical path. The difference between the outputs is used to eliminate the effects of a variation in the background signals and variations due to the thermal drift. This kind of construction makes the detector large and expensive and also difficult to construct for several different gases.

The patent U.S. Pat. No. 5,296,706 refers e.g. to those two patent publications mentioned above, and also describes, as a prior art, a further developed version of the latter patent provided a multiple of paired thermopiles and with an aperture sheet placed over the optical filters for analysis of several gas components in the gas mixture. This now discussed US-patent discloses a topography, which allows several channels to be used as independent analytical channels for detecting the absorption of a plurality of predetermined wavelengths. For this purpose the patent suggests separate reference thermopiles, which are identical with the active analytical thermopiles and are located behind these active thermopiles receiving the thermal radiation. Each reference thermopile and its corresponding active thermopile are disposed back to back in "parallel opposed" fashion with shielding means such as aluminum foil therebetween, whereupon the reference thermopiles are protected from all incident radiation. Each reference thermopile produces a signal representative of ambient temperature transients, the corresponding active thermopile produces a signal representative of the received radiation and ambient temperature transients, and these signals are processed to produce a combination signal with an intention that the effect of said thermal transients were eliminated, unlike in the arrangement of the U.S. Pat. No. 5,081,998. This kind of analyzer can be constructed for analysis of several gases but the thermopile structure is very complicated and expensive. Additionally the suggested calculations using a second order polynomial equation having cross product terms to calibration and compensation is considered to be a complicated task. Thermal gradients may also affect the thermopiles of the pair differently thus still inducing an offset in the signal. The patent U.S. Pat. No. 6,277,081 refers to the last mentioned two patent publications, too. Aiming to analyze carbon dioxide and more than five further anesthetic gas components, the suggested apparatus comprises a plurality of independent detectors provided with optical filters having particular wavelength transmissions for different gases, and also a plurality of reference detectors provided with further optical filters having particular wavelength transmissions for optical references. Additionally, the apparatus comprises at least one detector with an opaque optical filter to prevent substantially all radiation from reaching this blocked detector, and the number of these blocked detectors is fewer than said independent detectors. A large DC offset voltage is described as typical for all the detectors in an analyzer in the absence of any infrared radiation, and a specific mathematical compensation is applied after calibration. No attempt has been made to minimize said offset. As said "dark" offset signal is described to be typically 2 to 6 times the measurement signal received, the offset certainly has considerable influence on the reliability of the sensor between calibration events and during start-up.

Further the patent U.S. Pat. No. 5,542,285 discloses different means for compensating the thermal errors by describing a gas analysis apparatus in which compensation is provided for transient errors caused by temperature changes associated with said apparatus, said apparatus comprising: a sample cell containing the gas to be analyzed; an electromagnetic radiation source for passing electromagnetic radiation through the sample cell; a thermal detector having a radiation detecting sensor element receiving the radiation exiting said sample cell, said thermal detector having a reference sensor element protected from said radiation, said thermal detector generating an output signal indicative of a property of the gas in the cell, changes in the temperature of the thermal detector introducing errors in the output signal; temperature sensing means providing a temperature signal indicative of the temperature of the reference sensor element; and signal processing means coupled to said sensing means for determining the rate of change of temperature of said reference sensor element as a function of time and providing a compensating signal indicative of same, said signal processing means being coupled to said thermal detector and for altering the output signal of said thermal detector in accordance with the compensating signal to provide a temperature compensated output signal indicative of the property of the gas in said cell.

As to the measuring principle of the analyzers described above, it should be noticed that the actual target for measurement is the gas mixture, more specifically some of the gas components with variable concentrations and their absorptions, which are variable accordingly. The concentrations, not temperatures are the object for the measurement. The radiation sources are neither the target nor the object for measurement, because they should not be variable, but the temperature of these IR-sources shall be as constant as possible.

The patent U.S. Pat. No. 5,012,813 discloses a tympanic temperature measurement device to provide accuracy within one-tenth of a degree over limited ranges of ambient temperature and accuracy to within one degree over a wide range of ambient temperatures. The radiation detector for detecting the temperature of the tympanic membrane area at about the body temperature of a patient according to the patent comprises: a thermopile having a hot junction and a cold junction, the hot junction being mounted to view a target source; a temperature sensor for sensing the temperature of the cold junction; an electronic circuit coupled to the thermopile and responsive to the voltage across the thermopile and a temperature sensed by the temperature sensor to determine the temperature of the target, the electronic circuit determining the temperature of the target as a function of the voltage across the thermopile and the temperature of the hot junction of the thermopile determined from the cold junction temperature and a thermopile coefficient; and a display for displaying an indication of the temperature of the target determined by the electronic circuit. The electronic circuit determines the temperature of the target source from the relationship $T_T^4=(Kh \times H)+T_H^4$ where $T_T$ is the target temperature, Kh is a gain factor, H is a sensed voltage from the thermopile and $T_H$ is the hot junction temperature of the thermopile. Further according to the patent, the thermopile is positioned within a rear volume in a can of high conductivity material. The can comprises a radiation guide with a tapered form and with a germanium window at the front end, an additional conductive thermal mass surrounding the can and said rear volume, and a conductive plug attached to the rear end of the thermal mass and also surrounding the volume. The can is filled with a gas of low thermal conductivity such as Xenon surrounding the thermopile. The radiation guide is formed of a single piece of high conductivity material such as copper. Both the additional conductive thermal mass and the conductive plug are of a high conductivity material such as copper, too, and they are in close thermal contact with the can and with each other. According to the patent the output of the thermopile is a function of the difference in temperature between its warm junction, heated only by radiation viewed through the window, and its cold junction, which is in close thermal contact with the can, whereupon the radiation guide should be, throughout a measurement, at the same temperature as the cold junction. The patent does not describe how this close thermal contact with the can is achieved; the thermopile seems to be without any contacts in the center of said rear volume. The temperature of the cold junction is anyway monitored by a separate thermistor positioned within the conductive plug, and the signal voltage from the thermopile corrected respectively. Disclosed is that to minimize the temperature changes, the radiation guide and the can are well insulated by means of a casing of plastic material having low thermal conductivity and an insulating air space, but a high conductance thermal path is provided between the foremost end of the radiation guide and the portion of the can surrounding the thermopile to distribute any changes in temperature rapidly to the cold junction to avoid thermal gradients. This high conductance of the thermal path is enhanced by the unitary construction eliminating any thermal barriers. So, here the radiation source itself being independent from the measuring apparatus is the target, the temperature of which is measured as the object.

Further developments to the probe of this patent mentioned above is disclosed in patent U.S. Pat. No. 5,445,158. Here too, the thermal mass is of unitary construction which eliminates thermal barriers between the tube and the portion of the thermal mass surrounding the thermopile, and a plug of high thermal conductivity material positioned behind the thermopile is in close thermal contact with the mass. The outer sleeve is formed of low thermal conductivity plastic and is separated from the mass by an insulating air space. The taper of the mass increases the insulating air space adjacent to the end of the extension while minimizing thermal resistance from the tube to the thermopile. The rings, the window and the header are thermally coupled by high thermal conductivity epoxy. This way the thermal RC time constant for thermal conduction through the thermal barrier to the thermal mass and tube is at least two orders of magnitude greater than the thermal RC time constant for the temperature response of the cold junction to heat transferred to the tube and thermal mass. The RC time constant for conduction through the thermal barrier is made large by the large thermal resistance through the thermal barrier and by the large thermal capacitance of the thermal mass. The RC time constant for response of the cold junction is made low by the low resistance path to the cold junction through the highly conductive thermal mass, and the low thermal capacitance of the stack of beryllium oxide rings to the thermopile. Besides the transfer of heat from the environment, another significant heat flow path in the system is through the leads. To minimize heat transfer through that path, the lead diameters are kept small and the leads are trimmed off in the region. A pair of 40 gauge wires—0.079 mm diameter, respective cross sectional area of 0.0049 mm$^2$—are soldered to the shortened leads formed of 20 mils of kovar providing structural support to the thermopile assembly. The wires extend from the region through the plug and conduct thermopile signals to the electronics. Further potential heat flow path in the system is through the header to the plug. Since the header is in close thermal contact with the thermopile cold junction, any thermal gradients through the header would be amplified 100 to 1000 times by the thermopile producing large error signals. To eliminate the same an insulating region of air is provided behind the header to heat transfer through that path. Thus, any thermal gradients in the plug would be forced to travel through the mass and would be substantially dissipated without affecting the thermopile. In addition to the germanium window at the front end of the probe, two different embodiments with either a silicon window or no window at the front end of the probe are disclosed.

The common general feature of the probes in accordance with both U.S. Pat. No. 5,012,813 and U.S. Pat. No. 5,445, 158 is that radiation is measured from the tympanic membrane area at about body temperature. The wavelength region is equivalent to that of the transmission of germanium, about 1.8–23 μm, or to that of the transmission of silicon, about 1.1–40 μm, or without any limits in embodiments having no window. This gives a signal that well reflects the blackbody radiation or respective temperature of the patient's body. The amount of radiation is small but the very broad wavelength region still gives a fair signal, especially with the special elongated thermally conducting tube around the thermopile.

SUMMARY OF THE INVENTION

It is an object of the present invention to overcome the shortcomings of the above described prior-art techniques and to achieve a novel type of non-dispersive gas analyzer for eliminating offset and drift caused by thermal gradients in the analyzer. Especially it is an object of the present invention to eliminate the large offset signal caused by thermal radiation source induced static temperature gradient along the analyzer body not present in the temperature sensor without an internal source. Further it is an object of the present invention to achieve a small sized or miniature gas analyzer, which fulfills these objects, and in which also economic commercially available thermopile detectors may be used.

The invention is based on eliminating thermal offset and drift by minimizing the thermal gradients over the complete detector housing, including its electrical connections. This is attained by a gas analyzer in which the electrical wires are composed of materials and have dimensions producing an overall thermal conductance substantially lower than that of said electrical contact pins, the electrical wires are connected with the electrical contact pins either directly or indirectly, and enclosed in the thermal mass together with said detector housing(s), and the electrical wires are extending from the cavity through the thermal mass to the outside thereof with at least one exit point at said outer surface. Theoretically, there should not be any signal offset in a thermopile without radiation reaching its sensitive area. In order to achieve this there must not be any temperature difference between the hot junctions in the sensitive area and the cold reference junctions of the thermopile. This further means that no thermal gradient can be allowed within the detector housing in spite of the relatively high heat flow and small thermal mass of the small sized analyzer. There will always be a gradient from the analyzer to the ambient but according to the invention this gradient is transferred away from the detector housing and its electrical connections. This is done by completely enclosing the detector housing in a material with good thermal conductivity. Additionally, the thermal energy flow through the electrical connections are minimized in the invention. In gas analyzers radiation is provided by a fixed source and the wavelength region for measurement is narrow, typically less than 300 nm. This gives selectivity between the absorption of different gases fed to the sample volume of the analyzer. The absorption signal is typically small and proper design of the detector end of the analyzer is very important in order to achieve reliability and fast response, which is attained in the analyzer of the invention. The analyzer according to the invention has very small dimensions and weight so that the analyzer unit with radiation source, measuring volume and thermal detector(s) can be fitted directly on an ordinary printed circuit board. The construction according to the invention is such that it is possible to use simple commercial thermopile detectors. No special features like shielded or partly shielded detectors are needed. This makes the gas analyzer very cost effective and simple.

The gas analyzer of the invention can be used for, e.g., monitoring the composition of the airway gases of a patient anesthetized for the duration of an operation, whereupon the gases to be determined can include carbon dioxide ($CO_2$), nitrous oxide ($N_2O$) as well as at least one anesthetic agent.

BRIEF DESCRIPTION OF THE DRAWINGS

In the following, the invention will be examined in more detail with reference to the accompanying drawings.

DETAILED DESCRIPTION OF THE INVENTION

Figures 1, 2:
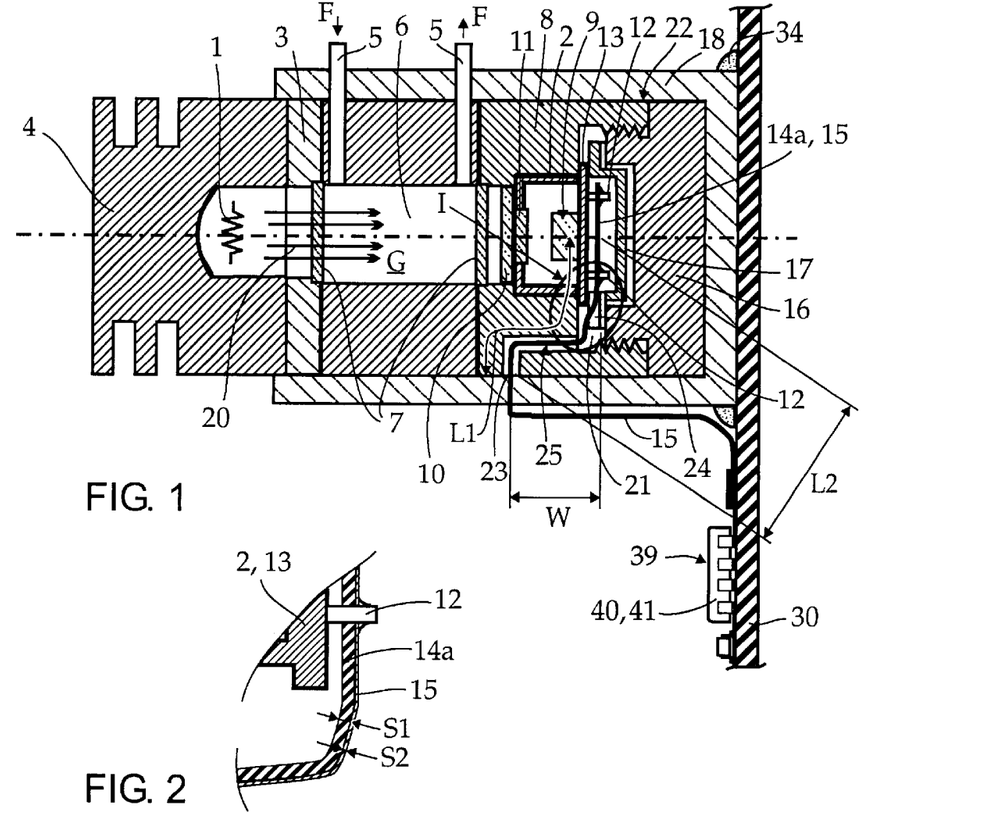
FIG. 1 illustrates the first embodiment of a small gas analyzer according to the invention seen in the longitudinal section of the analyzer parallel with the radiation beam, i.e. along the optical axis.
FIG. 2 shows the detail of the electrical wiring according the invention from the area I of FIG. 1 in an enlarged scale.
Figure 4:
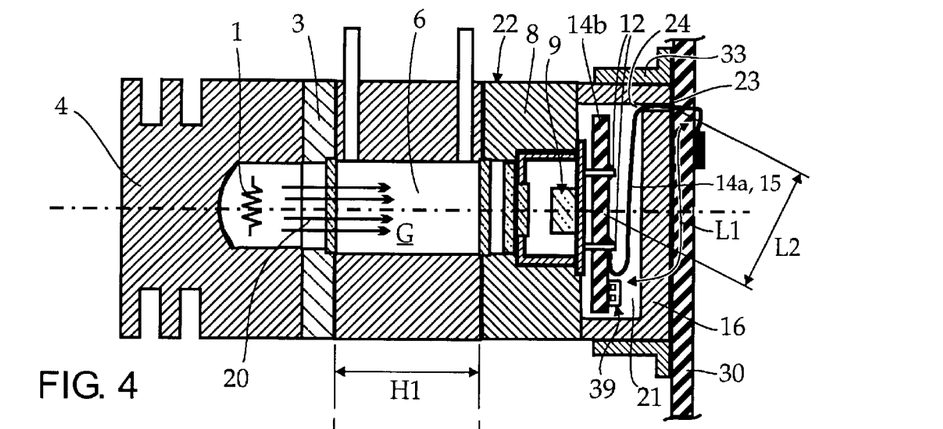
FIGS. 4 and 5 illustrate the second embodiment of a small gas analyzer according to the invention in the same view as in FIG. 1, and the corresponding thermal gradient through the analyzer between the radiation source and the detector end.
Figures 5, 6:
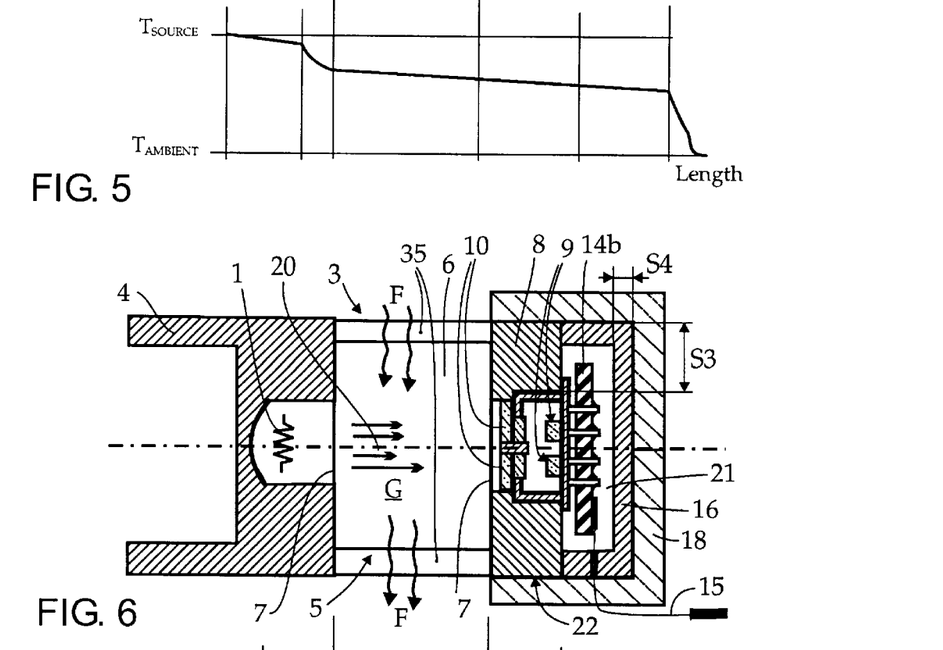
FIGS. 6 and 7 illustrate the third embodiment of a small gas analyzer according to the invention in the same view as in FIGS. 1 and 4, and the corresponding thermal gradient through the analyzer between the radiation source and the detector end.

The small sized or miniature gas analyzers for analyzing, e.g. measuring the concentration of one or several gas components are shown in figures. The analyzer comprises a measuring volume 6 between the infrared source 1 and the detector(s) 9, which volume has connections 5 for input and output flow of a sample gas mixture G. The measuring volume 6 can be a closed measuring chamber with inlet tube or tubes and outlet tube or tubes functioning as the connections 5 for the flow F of the gas mixture G into and out of the chamber, as shown in FIGS. 1 and 4. Alternatively the measuring volume 6 can be a generally open space, i.e. a substantially non-bordered room open to ambience, whereupon the flow F of the gas mixture G into and out of this non-bordered room is caused e.g. by natural movements in the surrounding atmosphere, as shown in FIG. 6. In this latter case the radiation source 1 is connected and supported by supports 35 with the rest of the analyzer, which supports are coarse or thin enough so as not to disturb said flow F. This way the gas mixture with at least one gas component, which is to be analyzed for determining its concentration in said mixture, is fed into the measuring volume through the connections 5. The measuring volume has first and second ends 7 transparent to radiation. Concerning the embodiment provided with the measuring chamber these transparent ends 7 are typically two windows forming the ends of the volume 6, as shown in FIGS. 1 and 4, and concerning the embodiment provided with the non-bordered room these transparent ends 7 can be the absence of a solid material, as shown in FIG. 6, but defined by the exit side of the optical system for the radiation source 1 and the incident side of the optical system for the detector(s) 9. The two windows forming said ends 7 are made of a material that transmits the infrared radiation used for the gas measurement. Typical window materials can be sapphire or calcium fluoride. The chamber forming the measuring volume 6 can be made of glass or preferably of metal for fast temperature stabilization and increase of thermal mass, but it can also be made of other suitable materials like polymers for better thermal insulation between the source and the detector. The length of the measuring volume 6 depends on the application and concentration range to be measured. For carbon dioxide in patient breathing gas the length H1 of the volume 6 is normally 3 mm–10 mm. Since a thermal contact between the built-in radiation source 1 and the detector 9 exists in all these versions of the gas analyzers, the same problems are still present.

A radiation source 1 is arranged in the analyzer to providing a beam 20 of electromagnetic radiation having a wavelength range. Preferably the beam 20 approaches collimation and is directed to pass said measuring volume through the first and second ends thereof. The collimated beam means parallel rays whereas a focused beam means rays radially diverging from or converging to a point or a surface. It shall be understood that no actual beam is ideal, and so a slight deviation of at maximum ±10°, or at maximum ±5° from the mean direction, i.e. from the axis of the collimated beam may be allowed. Anyway the deviation should be as small as possible and the rays as parallel as possible. The infrared source 1 is in most cases a broadband emitting hot filament, which has a temperature of at least 300° C. The radiation source can be in the form of a heater wire or a small light bulb depending on the required wavelength region. The source can be equipped with a concave mirror and/or a lens or lenses to collimate the radiation as indicated in the figure. Common to all these radiation sources 1 is that they produce heat. Part of the heat can be dissipated to the surroundings using a suitable heat sink 4, which surrounds largely said radiation source, but allows exit of said radiation beam 20. The heat sink can be a separate block of metal, which is in contact with or close to the radiation source like the bulb, or the heat sink can be machined and internally polished to form the concave collimating mirror. The outer surfaces of the heat sink 4 can be designed to comprise e.g. cooling fins for enforced convection, and can be blackened to enforce the radiation of the dead temperature. The cooling can be further enforced by a fan, not shown in the figures.

Regarding this invention the detector section of the gas analyzer is the most significant. This section comprises at least one thermal detector 9 having an active radiation detecting sensor element within at least one detector housing 2 and receiving the radiation exiting the measuring volume 6, and the thermal detector has a reference sensor element within the same detector housing 2 and protected from said radiation. The thermal detector 9 generates an output signal indicative of a property of said at least one gas component of said mixture in the measuring volume. This property of the at least one gas component is radiation absorption of said gas component over a predetermined wavelength band. The thermal detector 9, mostly a thermopile, can be purchased as mounted in a standard metal housing 2. Such thermopile detectors are provided e.g. by PerkinElmer™ Optoelectronics, Santa Clara, Calif. The typical modern thermopile is manufactured using standard silicon wafer technology with micromachining. The two different thermoelectric materials can be two different metals like bismuth and antimony but they can also be differently doped silicon. The conductors of these two thermoelectrically different materials have typically two set of junctions, one set of junctions in the center of a membrane with an infrared absorbing layer, called hot junctions, and the other set of junctions above the edge of the silicon substrate, called cold junctions. The substrate chip is mounted with good thermal contact to the base plate 13 of the detector housing 2, which is provided with electrical contact pins 12 for the output of the measuring signal(s). The incoming infrared radiation from the source 1 is absorbed at the hot junctions while the cold junctions are supposed to remain at the constant temperature of the base plate 13. The signal from the thermopile is directly related to the temperature difference between the hot and the cold junctions. Thus, with no incoming radiation the temperature difference should ideally be zero. Consequently, the signal should also be zero. However, in practice this may not be the case because the cold junctions are at a different temperature than the hot junctions even when the analyzer is in equilibrium because of the temperature gradient between the source 1 and detector section. The situation is made even worse by the fact that the electrical connections from the detector housing in prior art is connected directly to a printed circuit board 30 at ambient temperature.

The detector section also comprises at least one optical bandpass filter 10 between said active radiation detecting sensor element and said measuring volume 6. The typical detector housing(s) 2 have a detector window 11 or windows 11 side by side, and the optical bandpass filter 10 can be integrated into the detector housing and would then substitute the window(s) 11. These kinds of detectors are commercially available. Of course one or several separate optical bandpass filter 10 can be arranged in front of the detector housing in the radiation beam. For conventional infrared gas measurements with fair selectivity the bandwidth of such a bandpass filter is typically between about 50 nm and 300 nm. A broader bandwidth would only increase the total signal level without increasing the absorption from the gas to be measured. As a consequence, the signal would become very non-linear and larger concentrations would be very difficult to measure with precision, especially if the thermal gradients also influence the measurement. A narrower bandwidth can be used if the signal intensity is high enough. In some special cases it may even be advantageous to use a bandwidth of only about 10 nm, but for the radiation absorption of a gas component the predetermined wavelength band has preferably a width of at maximum 400 nm.

Further part in the detector section is, according to the invention, a combined thermal mass 8, 16 formed of a material having high thermal conductance. The combined thermal mass 8, 16 has a cavity 21 for the housing(s) 2 of the detector(s) 9 and an outer surface 22, whereupon the thermal mass surrounds at least said detector housing in the cavity and is in contact with the detector housing. The good thermal contact between the combined thermal mass 8, 16 and the detector housing 2 ensures fast thermal settling in the gas analyzer. The thermal mass 8, 16 also extends towards the radiation source 1, at minimum around the second end 7 of the measuring volume 6, which is away from the radiation source and at maximum around the first end 7 of the measuring volume 6, which is nearest to the radiation source, whereupon the second end can be also called as a distal end and the first end as the proximal end of the measuring volume. The combined thermal mass disclosed above has a peripheral section 8 with a material thickness S3 and a bottom section 16 with a material thickness S4, which thicknesses S3, S4 are at minimum 2 mm, and at maximum 10 mm, or preferably at maximum 5 mm in the small sized gas analyzer of the invention.

As a summary, part of the heat produced by the radiation source 1 is so dissipated to the surroundings using a suitable heat sink 4 but, inevitably, heat will also be conducted along the analyzer body towards the detector housing 2. In other words, there will be a temperature gradient between the radiation source and the detector housing and, further, the surroundings at ambient temperature. Also other thermal gradients may occur mainly as a consequence of changing ambient conditions. These are dynamic gradients because they level out with some time constant. However, the main static gradient has its origin in the infrared source. In order to decrease the heat flow from the infrared source 1 to the rest of the analyzer it is common practice to thermally insulate the source. This is done by arranging a thermal barrier 3 between the heat sink 4 and the thermal mass 8, 16. The thermal barrier 3 can be attained by adding an insulating material with low thermal conductivity between the infrared source and the rest of the analyzer, as shown in the FIGS. 1 and 4. This alternative is practical in cases where the measuring chamber is used for the measuring volume 6. The thermla barrier 3 can be attained by leaving a substantial space H2 between the infrared source and the rest of the analyzer, as shown in the FIG. 6, whereupon the thermal barrier is formed by lack of material. This alternative is practical in cases where the non-bordered room open to ambience is used for the measuring volume 6. Despite of these measures there will always be a static thermal gradient inside the analyzer.

Figure 3:
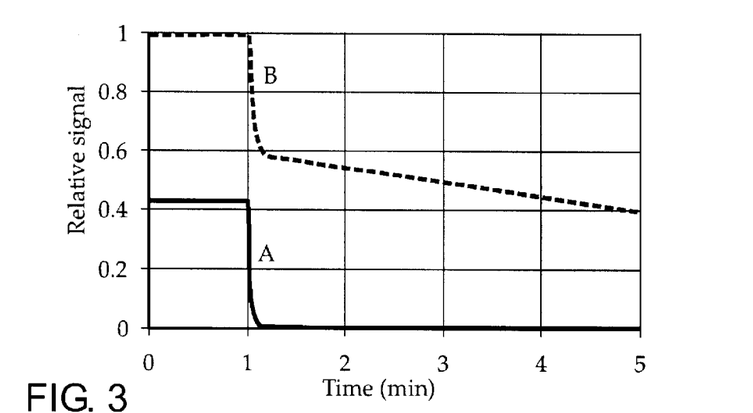
FIG. 3 shows the temporal variation of the relative signal A from a gas analyzer according to the invention and the relative signal B according to prior art, after the disconnection of the radiation source.
Figure 8A:
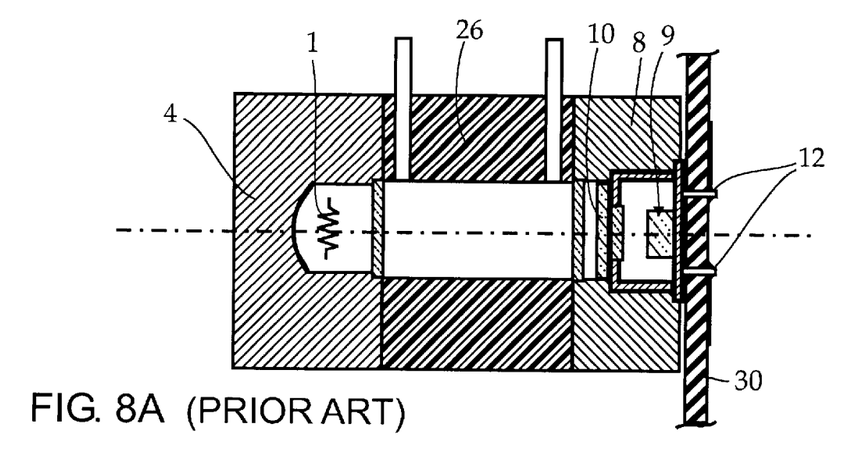
FIGS. 8A and 8B illustrates a typical gas analyzer according to prior art, and the thermal gradients through the prior art analyzer between the radiation source and the detector end respectively.
Figure 8B:
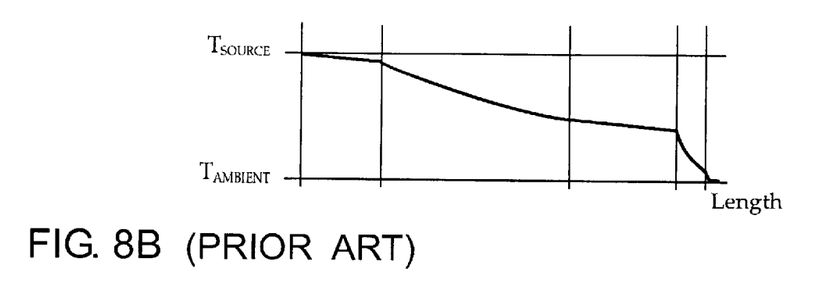

Now to the prior art situation. Such a gas analyzer with some parts similar to those illustrated in FIGS. 1, 4 and 6 is shown in FIG. 8A. Here the gas analyzer comprising a radiation source 1 with a heat sink 4, a measuring chamber 26 made of a plastic or a polymer, optical filter 10 and a thermopile detector 9 enclosed in a peripheral thermal mass 8, is fitted directly onto a printed circuit board 30 utilizing the contact pins 12 of the detector housing, the printed circuit board 30 being directly facing ambient conditions according to established practice. Further electrical connections from the board 30 to amplifiers and other monitor electronics are also present, but not shown in the figure. FIG. 8B is a diagram showing the temperature gradients inside the prior art analyzer with reference to the different parts of it. The heat sink 4 is supposed to be at the temperature $T_{SOURCE}$ and the temperature decreases towards the ambient temperature $T_{AMBIENT}$ as a function of the distance along the analyzer. The heat sink 4, and thermal mass 8 are supposed to be made of metal, e.g. aluminum or copper. The temperature drop across these metal parts is seen to be rather small. A larger temperature drop occurs across the measuring chamber 26 and also across the printed circuit board 30 with its connections 12 to the thermal detector 9. This means that there is a considerable thermal gradient across the detector housing and, consequently, over the thermal detector 9 itself. The temperature of the heat sink $T_{SOURCE}$ can typically be about 50° C., which means that the total gradient is about 25° C. between the ends of the analyzer. A typical silicon thermocouple develops about 400 $\mu$V/K. If one assumes 40 thermocouples in the thermopile detector 9 it means an output signal of 16 mV/K. A typical carbon dioxide patient analyzer would give an output signal of about 2 $\mu$V for the smallest measurable concentration 0.1% by volume. This would correspond to a temperature difference in the thermopile of only about 0.13 mK. A much higher temperature difference results from a construction like the one in FIG. 8A. This means that the signal would have a considerable offset even under stable conditions. The situation is shown in FIG. 3 as the dashed curve B. The signal level without gas absorption has an arbitrary value of 1 unit in a stable situation. After 1 minute the infrared source is disconnected. As can be seen the signal does not approach zero as expected but a value about half of the initial or possibly even more. In FIG. 3 the signal offset is about 0.6 units and it very slowly approaches zero as the analyzer cools down to ambient temperature. It may be possible to calibrate the analyzer to compensate for this offset but the exact value is difficult to assess because of the slow drift demonstrated e.g. after the infrared source has been switched off.

According to the invention the problems in the prior art gas analyzers are solved by making the thermal gradient across the complete peripheral thermal mass 8 as small as possible, i.e. by making the thermal gradient to approach zero. This means that also no direct contact between the detector 9 and the printed circuit board 30 is present in the analyzer. For this purpose the backside of the analyzer is covered by a bottom section 16 of a material having high thermal conductance, like the peripheral section 8 and its material. The material with high thermal conductance can be a metal like silver or copper or aluminum or also a non-metallic material like a ceramic, but aluminum is are best suited for practical reasons. To accomplish this bottom section 16, e.g. a metal lid, is attached to the peripheral section 8 using for instance a thread as in FIG. 1, or a face-to-face contact as in FIGS. 4 and 6, or in some other suitable way, the only requirement being good thermal contact with the section 8. The detector has to react fast to changes in temperature and settle to a new equilibrium. This requires a good thermal contact between the detector housing 2 in the cavity 21 and the combined thermal mass 8, 16. The detector housing can be glued or mechanically clamped in place or it can be pressed down using the threaded lid 16 as in FIG. 1. In that case some kind of flexible spacer 17 must additionally be used to allow for tolerances.

Further according to the invention the problems in the prior art gas analyzers are solved by arranging the gas analyzer to comprise electrical wires 15 with special dimensions and configuration between the detector 9 and e.g. an outer printed circuit board 30 or any further electrical connections. These electrical wires 15 are firstly composed of materials and have dimensions producing an overall thermal conductance substantially lower than that of said electrical contact pins 12 in the detector housing, and secondly these electrical wires 15 are connected with the electrical contact pins 12 either directly or indirectly. This direct connection means that the electrical wires 15 of the invention are in galvanic contact with the contact pins and go then through some portion of the thermal mass 8, 16. The indirect connection means that the electrical wires 15 go via an inner printed circuit board 14b having galvanic connections as well. These can be called as a galvanic transmission. Alternatively the indirect connection means that the electrical wires 15 form e.g. a coil in the cavity 21, whereupon there is provided an electromagnetic transmission between the coil and electronic circuits on an outer circuit board 30. This latter transmission is a non-galvanic and passive transmission. It is also possible to provide a non-galvanic and active transmission between the electrical wires 15 being solely in the cavity by radio frequencies, but this means quite complicated arrangements. These non-galvanic transmissions require use of a ceramic for at least a part of the thermal mass 8, 16. If used the inner printed circuit board 14b is fastened to said electrical contact pins and enclosed in the thermal mass together with said detector housing(s), i.e. the inner printed circuit board 14b is positioned in the cavity 21 within the combined thermal mass 8, 16. The electrical wires 15 then extend from the cavity 21 through the thermal mass 8, 16 to the outside thereof, whereupon the wires 15 has at least one exit point 23 at the outer surface 22, as shown in the figures. It shall be understood that there is at least two electrical wires 15 to conduct the signal from the detector to the next electrical/electronic circuits for signal processing, but there could also be several electrical wires 15 for signals especially in cases when multiple detectors 9 for reference purposes and/or for analysis of two or more gas components is utilized, that there can be also electrical wires 15 for feeding of voltage/current for possible electrical and/or electronic circuits 39 in cases when this kind of components are included on the internal printed circuit board 14b, and that these several electrical wires can have separate exit points 23 at the outer surface 22. The inner printed circuit board 14b can be either a stiff board generally used in ordinary electronic devices or a flexible printed circuit board, e.g. similar to or of the same type as the flexible printed circuit board 14a used for the electrical wires 15.

According to a specific principle of the invention the overall thermal conductance of the electrical wires 15 is at maximum 1/10th of the overall thermal conductance of the contact pins 12 in the detector housing, and in practice a thermal conductance of at maximum 1/20th or smaller than 1/40th of the overall thermal conductance of the contact pins is possible. The first means to this goal is that the electrical wires 15 have a mean length L1 substantially greater than the mean distance L2 between said electrical contact pins and said exit point(s) 23. The electrical wires 15 have of course also input point(s) 24 from the cavity into the thermal mass 8, 16 to enable extending of the wires from inside the cavity to outside thereof. The proportions mentioned above and below are achieved by providing supplementary portions 25 for the lengths L1 of said electrical wires between the input point(s) 24 and the exit point(s) 23 in thermal mass 8, 16, whereupon a substantially curved or serpentine configuration of the wires is formed. In the first alternative the angled or curved or serpentine configuration is formed between the cavity 21 and the outer surface 22 due to distance(s) W in direction of the outer surface of said thermal mass 8, 16 between each of the input points and each of the respective exit points. This means at least one loop within the combined thermal mass, as shown in FIG. 1. In the second alternative the curved/serpentine configuration is formed between the contact pins 12 of the detector housing 2 and the input point(s) 24 from the cavity into the thermal mass 8, 16. This means a loop or loops within the cavity 21, as shown in FIG. 4. Most effective is to guide the electrical wires 15 some distance inside the thermal mass 8, 16 towards the higher temperature of the infrared source like in FIG. 1. The supplementary portions 25 in the lengths L1 of the electrical wires 15 causes the total length L1 of the electrical wires to be at least 15%, or preferably at least 30%, or typically at least 60% longer than the distance L2 between said electrical contact pins 12 and said exit point(s) 23. The second means to this goal is that the electrical wires 15 are integral wirings on a flexible printed circuit board 14a with small cross-sectional dimensions, which flexible printed circuit board 14a is fastened e.g. by soldering or welding or by an electrically conductive adhesive or the like either directly to the contact pins 12 or to the inner printed circuit board 14b. The board thickness S1 of this thin flexible board or base material is at maximum 0.4 mm, or preferably at maximum 0.2 mm, and the wiring thickness S2 of the electrical wires 15 on the flexible base material is at maximum 70 μm, or preferably at maximum 40 μm, whereupon the width of the wiring is typically between 0.1 mm and 0.3 mm. The connecting electrical wires 15 have typically a cross-sectional area at maximum 0.02 mm². Any other type of electrical connection can be used, if only a low enough thermal conductance is achieved, as defined above.

By totally enclosing the detector housing 2 in the combined thermal mass 8, 16, and by using connecting electrical wires 15 with an extremely low thermal conductance, achieved by minimal cross sections S1, S2 of the connecting wires and/or by substantially extended length like supplementary portions 25 of the connecting wires, the thermal influence of the connection between the detector(s) 9 is minimized. The curved/serpentine configuration of the wires 15 provides the advantage of preheating the electrical connections before they come into contact with the contact pins 12 of the detector housing 2. The thermal situation is shown in FIG. 5. The temperature gradient curve deviates from that of FIG. 8B in such a way that the slowly declining gradient inside the thermal mass extends well beyond the detector housing and all the way to the outer surface 22, or end surface of the bottom section 16 of the thermal mass. Only after that point follows the steep gradient towards $T_{AMBIENT}$. This gradient no longer influences the behavior of the detector and, as a consequence, the signal offset decreases dramatically depending now only on the gradient inside the thermal mass 8, 16.

Figure 7:
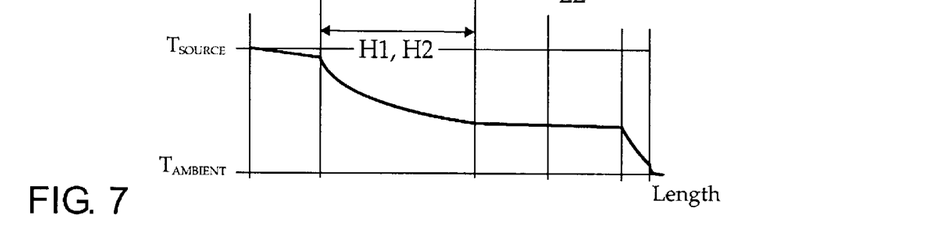

A further improvement results if a thermal insulation 18, which surrounds at least said thermal mass 8, 16, i.e. both the peripheral section 8 and the bottom section 16 on all sides thereof, is added to the gas analyzer further of the invention, as shown in FIGS. 1 and 6. In case the measuring volume 6 is the closed measuring chamber, the thermal insulation 18 preferably extends to surround this measuring chamber, and in the most preferred arrangement the thermal insulation 18 extends to surround the thermal barrier 3 between the heat sink 4 and the thermal mass 8, 16, as shown in FIG. 1. The temperature gradient across the peripheral and bottom sections 8, 16 will then almost disappear and also the influence from changes in temperature will slow down, as can be understood from the curve in FIG. 7. The signal behavior in the gas analyzer according to the invention is shown as curve A in FIG. 3. The offset has practically disappeared. No slow drift occurs in the dark signal but it stays close to zero as it should according to theory. With reference to FIG. 7 the steep temperature gradient, which is substantially similar for the gas analyzer of FIG. 1, between the thermal mass 8, 16 and $T_{AMBIENT}$ will mostly be formed inside the thermal insulator 18. As a comparison, the addition of such a thermal insulation to the prior art analyzer in FIG. 8A would not much improve the offset behavior, but would still leave a disturbing gradient within the thermal mass. According to the invention a complete enclosure of the back side of the detector housing 2 into a material of good thermal conductance and in good thermal contact with the rest of the thermal mass 8, 16 is a demand. Thermal insulation 18 mainly slows down and thus decreases the dynamic thermal behavior of the analyzer, but it also has a decreasing influence on the thermal gradient over the detector housing.

The gas analyzer according to the invention can comprise additional features, which further enhance the accuracy and reliability. The inner printed circuit board 14b fastened to the electrical contact pins 12 can comprise e.g. first electrical and/or electronic circuits 39, which are electrically attached between said contact pins and said electrical wires. These electrical and/or electronic circuits 39 can be for instance signal amplifiers or any other circuit selected and considered practical. The gas analyzer further comprises an outer printed circuit board 30 comprising electrical and/or electronic circuits and components for further processing of said output signal(s). The thermal mass 8, 16 is attached either directly or preferably with the thermal insulation 18 between on said outer printed circuit board 30. This attachment can be performed by any known or new materials or method useful for the purpose, of which at least bonding with glue 34 and insertion in a mechanical holder 33 like a spring holder, can be mentioned.

In the gas analyzer of the invention the zero level, which means signal from the detector 9 in the absence of absorption, is fixed. This can be done either by feeding a gas or gas mixture, which does not certainly have absorption within the wavelength band used for measuring the concentration of the interesting gas component, into the measuring volume 6, and then detecting and storing the data, or by performing a measurement with the interesting gas mixture G in the measuring volume 6 through a reference filter having an absorption band, which deviates from the absorption bands useful for concentration measuring purposes means, and then detecting and storing the data. The zero level so concerns a first reference signal level respective to lack of any absorption in said gas mixture G, and the detection and storing can be performed using e.g. one of the at least two optical bandpass filters 10 and/or using one or several electronic circuits 40. Further in the gas analyzer of the invention the dark level, which means signal from the detector 9 in the absence of any radiation, is fixed. In the inventive gas analyzer the dark level can be considered to be zero, because due to the elimination of the thermal gradients within the detector housing 2 there is no significant signal under conditions without radiation from the radiation source 1. The dark level so concerns a second reference signal level respective to lack of any radiation into said thermal detector 9, and meaning also infinite absorption in the gas mixture, which reference signal being substantially zero or approaching zero can be stored in one or several electronic circuits 41 if needed for calculations of the concentration(s). There is nothing to prevent the detection of this dark level signal if there is a need for checking it, and this operation can be performed by switching off the radiation source momentarily or by shading the detector(s) 9 with a non-transparent element between the radiation source and the detector, and the dark level, if found, can be stored in one or several electronic circuits 41. This checking of the dark level can be activated e.g. using said one or several electronic circuits 41. However, this procedure may be slow especially if the source is slow or the procedure may otherwise be unnecessarily complicated, so the preferable method is to consider the dark level to be zero. Anyway the second reference signal level has a value, which can be neglected in the gas analyzer according to the invention. The introduced gas concentration error is normally negligible because the gas absorption never comes very close to complete absorption with properly chosen construction parameters.

The invention is particularly suited to applications in which the infrared radiation intensity within a narrow wavelength region is determined by direct or indirect measurement of the temperature difference produced between the sensor element receiving the impinging radiation and a reference element. Such a detector has the inherent shortcoming that a persisting or changing thermal gradient may disturb the internal balance of the detector, and consequently, the output signal will contain an offset error, which degrades the accuracy of the gas analyzer. The thermal detector used in the measurement may advantageously be a thermopile detector. The method according to the invention is suited for use in gas analyzers designed to perform identification or measurement of the concentration of at least one component of a sample gas mixture.

In the description above some preferred embodiments of an improved non-dispersive infrared gas analyzer have been presented. It will be understood by those skilled in the art that various changes in details may be made without departing from the spirit and scope of the invention as defined by the appended claims.

What is claimed is:

1. A gas analyzer comprising:
   a measuring volume having connections for input and output flow of a sample gas mixture, at least one gas component of which is to be analyzed for determining its concentration in said mixture, and having first and second ends transparent to radiation;
   a radiation source for providing a beam of electromagnetic radiation having a wavelength range, said beam approaching collimation and being directed to pass said measuring volume through the first and second ends thereof;
   a heat sink for said radiation source;
   at least one thermal detector having an active radiation detecting sensor element within at least one detector housing and receiving the radiation exiting said measuring volume, said thermal detector having a reference sensor element within the same detector housing and protected from said radiation, said thermal detector generating an output signal indicative of a property of said at least one gas component of said mixture in the measuring volume;
   at least one optical bandpass filter between said active radiation detecting sensor element and said radiation source;
   electrical contact pins in said at least one detector housing for the output of said signal(s);
   electrical wires composed of materials and having dimensions producing an overall thermal conductance substantially lower than that of said electrical contact pins, said electrical wires being connected with the electrical contact pins either directly or indirectly, and enclosed in the thermal mass together with said detector housing(s), and extending from the cavity through the thermal mass to the outside thereof with at least one exit point at said outer surface;
   a thermal mass formed of a material having high thermal conductance, said thermal mass: having a cavity and an outer surface, surrounding at least said detector housing in the cavity, being in contact with said detector housing, and extending towards the radiation source; and
   a thermal barrier between the heat sink and the thermal mass.

2. A gas analyzer of claim 1, wherein said electrical wires have a mean length substantially greater than a mean distance between said electrical contact pins and said exit point(s).

3. A gas analyzer of claim 2, wherein said electrical wires have a length, which is at least 15%, or at least 30% longer than the distance between said electrical contact pins and said exit point(s).

4. A gas analyzer of claim 1, wherein said electrical wires have input point(s) from the cavity into the thermal mass, and there is/are distance(s) in direction of the outer surface of said thermal mass between each of the input points and each of the respective exit points providing supplementary portions for the lengths of said electrical wires between the input point(s) and the exit point(s) in thermal mass with a substantially curved or serpentine or angled configuration.

5. A gas analyzer of claim 4, wherein said electrical wires have supplementary portions of their lengths between the contact pins and input point(s) from the cavity into the thermal mass, providing a substantially curved or serpentine configuration.

6. A gas analyzer of claim 1, wherein said electrical wires are integral wirings on a flexible printed circuit board having:
   a board thickness at maximum 0.4 mm, or at maximum 0.2 mm, and
   wiring thickness at maximum 70 $\mu$m, or at maximum 40 $\mu$m.

7. A gas analyzer of claim 1, wherein said printed circuit board fastened to said electrical contact pins comprises first electrical and/or electronic circuits electrically attached between said contact pins and said electrical wires.

8. A gas analyzer of claim 1, wherein said measuring volume is a closed measuring chamber with inlet and outlet tubes, or a generally non-bordered room open to ambience.

9. A gas analyzer of claim 1, wherein said thermal detector is a thermopile.

10. A gas analyzer of claim 1, wherein said property of the at least one gas component is radiation absorption of said gas component over a predetermined wavelength band having a width of at maximum 400 nm.

11. A gas analyzer of claim 1, further comprising thermal insulation, which surrounds at least said thermal mass.

12. A gas analyzer of claim 7, wherein said thermal insulation extends to surround said closed measuring chamber.

13. A gas analyzer of claim 7, wherein said thermal insulation extends to surround said thermal barrier between the heat sink and the thermal mass.

14. A gas analyzer of claim 1, wherein said radiation source is a broadband emitting hot filament.

15. A gas analyzer of claim 1, wherein said radiation source has a temperature of at least 300° C.

16. A gas analyzer of claim 1, wherein said thermal mass has a peripheral section with a material thickness and a bottom section with a material thickness, whereupon said thicknesses are at minimum 2 mm, and at maximum 10 mm.

17. A gas analyzer of claim 1, wherein said overall thermal conductance of the electrical wires is at maximum $\frac{1}{10}$th of said overall thermal conductance of the contact pins.

18. A gas analyzer of claim 1, further comprising an outer printed circuit board comprising electrical and/or electronic circuits and components for further processing of said output signal(s), and said thermal mass is attached directly on said outer printed circuit board.

19. A gas analyzer of claim 11, further comprising an outer printed circuit board comprising electrical and/or electronic circuits and components for further processing of said output signal(s), and said thermal mass is attached on said outer printed circuit board with the thermal insulation between said thermal mass and said outer printed circuit board.

20. A gas analyzer of claim 1, further comprising:
   zero level means for detecting and storing a first reference signal level respective to lack of any absorption in said gas mixture; and/or optionally dark level means for detecting and storing a second reference signal level respective to lack of any radiation into said thermal detector.

21. A gas analyzer of claim 20, wherein said second reference signal level representing a dark level has substantially a value of zero, or a value to be neglected.

22. A gas analyzer of claim 1, wherein said thermal mass extends at minimum around said second end away from the radiation source and at maximum around said first end nearest to the radiation source.

23. A gas analyzer of claim 1, wherein said indirect connection between the electrical wires and the contact pins is through an inner printed circuit board fastened to said electrical contact pins.

24. A gas analyzer of claim 1, wherein said material of said thermal mass is a metal or a ceramic.

25. A gas analyzer of claim 10, wherein said thermal insulation extends to surround said closed measuring chamber.

26. A gas analyzer of claim 10, wherein said thermal insulation extends to surround said thermal barrier between the heat sink and the thermal mass.

* * * * *